United States Patent
Mariotti et al.

(10) Patent No.: US 7,708,938 B2
(45) Date of Patent: May 4, 2010

(54) METHOD AND DEVICE FOR MEASURING AND CONTROLLING THE CIRCULATION OF FLUIDS IN ENDOSCOPE CHANNELS

(76) Inventors: Bernard Mariotti, 77 rue Paul Codaccioni, Marseilles (FR) 13007; Frédéric Dray, 101 avenue de la Timone, Marseilles (FR) 13010

( * ) Notice: Subject to any disclaimer, the term of this patent is extended or adjusted under 35 U.S.C. 154(b) by 1505 days.

(21) Appl. No.: 10/506,682

(22) PCT Filed: Feb. 14, 2003

(86) PCT No.: PCT/FR03/00479

§ 371 (c)(1), (2), (4) Date: Dec. 22, 2004

(87) PCT Pub. No.: WO03/077960

PCT Pub. Date: Sep. 25, 2003

(65) Prior Publication Data

US 2005/0079094 A1   Apr. 14, 2005

(30) Foreign Application Priority Data

Mar. 20, 2002 (FR) ................................. 02 03439

(51) Int. Cl.
  *A61L 2/24* (2006.01)
  *B08B 9/00* (2006.01)
  *G01B 13/08* (2006.01)
(52) U.S. Cl. ................... 422/3; 134/22.12; 73/37.5
(58) Field of Classification Search ............... 422/33, 422/112, 3; 134/22.12; 73/37.5
  See application file for complete search history.

(56) References Cited

U.S. PATENT DOCUMENTS

| | | | | |
|---|---|---|---|---|
| 5,494,530 A | * | 2/1996 | Graf | 134/18 |
| 5,738,824 A | * | 4/1998 | Pfeifer | 422/3 |
| 2002/0064479 A1 | | 5/2002 | Nakanishi et al. | |
| 2002/0182105 A1 | | 12/2002 | Nakanishi et al. | |

FOREIGN PATENT DOCUMENTS

| | | |
|---|---|---|
| EP | 0945140 | 9/1999 |
| FR | 2705896 | 12/1994 |
| FR | 2803755 | 7/2001 |
| JP | 2002-065607 | 3/2002 |
| WO | 93/24046 | 12/1993 |

OTHER PUBLICATIONS

English Language Abstract of JP 2002-065607.

* cited by examiner

*Primary Examiner*—Sean E Conley
*Assistant Examiner*—Kevin C Joyner
(74) *Attorney, Agent, or Firm*—Greenblum & Bernstein, P.L.C.

(57) ABSTRACT

Method and device for measuring and controlling the circulation of fluids in endoscope channels. Device includes hermetic chamber having a known volume and a low level and high level sensor to control filling and emptying. The chamber is connected to a filtered air compressor, an injection pump to inject a drying product and a circulation pump to circulate cleaning and disinfecting solutions contained in the tank. The tank can receive at least one endoscope and includes injectors connected by a solenoid valve to the hermetic chamber. The device is used to verify and record the flow of cleaning, disinfecting, rinsing and drying solutions passing through each of the endoscope channels during the cleaning and disinfecting operations.

15 Claims, 1 Drawing Sheet

METHOD AND DEVICE FOR MEASURING AND CONTROLLING THE CIRCULATION OF FLUIDS IN ENDOSCOPE CHANNELS

CROSS-REFERENCE TO RELATED APPLICATIONS

The present application claims priority under 35 U.S.C. §119 of French Patent Application 02/03439, filed on Mar. 20, 2002, the disclosure of which is expressly incorporated by reference herein in its entirety.

BACKGROUND OF THE INVENTION

1. Field of the Invention

The invention relates to a method and a device for measuring and controlling the circulation of fluids in endoscope channels, directed to verifying and recording the flow of cleaning, disinfecting, rinsing, and drying solutions passing through each of the endoscope channels during operations adapted to clean and disinfect them.

2. Discussion of Background Information

Endoscopes 1 (FIG. 1) are apparatuses used in hospitals. They comprises a control box 2 at one of the ends of an exploration tube 3 adapted to be inserted through a natural conduit into an inner cavity of a patient's body in order to perform the diagnosis of lesions or certain treatments such as, for example, extracting foreign bodies, destroying tumors by coagulation or resection, introducing medicines or substances that are impervious to x-rays. The exploration head is connected by a second tube 4 to a proximal portion 5 comprising a series of injection couplings 6.

These are complex apparatuses comprising in a same tube optic fibers guiding the light coming from a generator, optic fibers carrying images or a video sensor (CCD), as well as various channels, such as operating channels, suction channel, air insufflation channel, water insufflation channel, erecting channel, washing channel. To make the endoscope compact, some of them can be joined in their downstream portion so as to form a single channel. For example, this may be the case for the air and water channels which form a common channel over the last centimeters of the insertion tube of the endoscope, and for the operating channels that join the suction channel. The flows circulating in the endoscope can also be mixed in a chamber (piston cage) having the same number of inlets and outlets.

The real difficulty in cleaning and disinfecting these apparatuses relates to these inner channels in which the circulation of the fluids can be non-existent or inefficient due to their diameter (0.5-4 millimeters). Insufficient pressure does not allow the passage of the solutions, and too much pressure can damage the channels. Furthermore, in view of the interrelation of the channels, it is difficult for the operator to ensure that the circulation of the fluids was sufficient in each channel portion. It is then impossible to ensure that the washing and disinfecting processes were efficient.

To ensure that the various commercially available cleaning and disinfecting processes are efficient, whether they are manual or automated, it is necessary to perform samplings in each of the portions of the channels. To this end, a trained technician (generally a hygienist or a pharmacist) circulates sampling solutions directed to a syringe. These solutions are capable of detaching germs that may remain on the walls of the endoscope channels, and of neutralizing possible disinfectant residues that could vitiate the sampling results.

This handling is constraining as it requires irrigating each of the inlets of the various endoscope channels, one after the other, with all of the possible risks of contamination associated with the handling. It also requires rinsing and disinfecting the endoscope again.

Due to the cumbersomeness of this handling and of the protocol associated therewith, and the need to use trained technicians, who often are in a limited number in the hospital, these samplings are rarely performed.

An automated system for cleaning and disinfecting flexible endoscopes has been previously described in the French Patent No. 2 705 896. It makes it possible to circulate the fluids in the outer portions of the endoscope, as well as independently in each of the inner channels of the endoscope. However, this system does not make it possible to automatically ensure that the cleaning/disinfecting/rinsing/drying fluids have indeed circulated in each portion of each channel. If the endoscope is incorrectly coupled to the automaton, or if the one or several channels are partially or completely closed, the flow and concentration of the cleaning/disinfecting/rinsing/drying solutions through the endoscope, as well as the dwell time can be substantially reduced or even eliminated, resulting in an incomplete disinfection of the instrument.

With respect to safety for the patient, this is currently the most significant flaw in machines of this type. That is the reason why the operators are required to first ensure that none of the channels is closed, and to verify at the end of the cycle that the channels are properly coupled.

Nonetheless, certain automatons have been equipped with flow meters or pressure sensors in order to control the flow or the pressure in each of the channels. All of these methods attempt to determine the volume circulating in the channels in a time unit. The volume is deducted from the interpretation of a measuring sensor (pressure drop, number of impulses of a wheel).

However, these solutions encounter a number of problems:

They are expensive, as they require as many sensors as channel portions to be controlled (up to 8 depending on the endoscopes).

In order to allow for an accurate control, the flow or pressure delivered at the inlet of the channels cannot be optimized. As a result, the control times are long, up to several minutes per channel controlled, which can increase the total time of the cycles.

They do not guarantee that a minimum volume corresponding to the saturation of the channel controlled has indeed circulated in the channel.

The diagnosis of a proper circulation in the channel only relies on the indications provided by a single sensor. The failure of this sensor can cause a serious diagnosis error.

Finally, they require frequent calibrations, and in view of the diverse types of channels, from one mark to the next, the adjustments of the thresholds turn out to be compromises. These adjustments set off false alarms that lead the users to frequently deactivate these safety mechanisms.

SUMMARY OF THE INVENTION

The device, which is directed to the present invention, ensures a limited number of devices not relying on the sensor interpretation, that the fluids circulate in each of the inner channels of the endoscope, with a flow that is well characterized and recorded during each of the endoscope cleaning, disinfecting, rinsing, and drying phases.

Due to a system that allows increasing the pressure of the flow passing through the endoscope channels and ensuring that a known solution volume has indeed circulated in said channels, and allows verifying and recording the flow in each channel at a given pressure, the invention makes it possible to ensure that each of them has indeed been cleaned, disinfected, rinsed, and dried by guaranteeing the presence of an adequate volume of the solution involved to saturate the channel for a predetermined period of time. It also makes it possible to use the optimum pressure and flow for each of the channels so as to ensure the optimum mechanical effect in the shortest time possible. Finally, the invention is directed for the user to have a quick and reliable access for sampling all of the portions of the endoscope inner channels, at the end of the cycle, in order to be able to analyze its possible state of contamination.

The device is constituted of a hermetic chamber having a known volume and provided with a low level and high level sensor allowing to control and record the filling and emptying thereof, and the upper portion of which is coupled to a filtered air compressor controlled by a pressure sensor, to a connection solenoid valve that allows air to evacuate while said chamber is being filled, to an injection pump that allows injecting a product promoting the drying, and to a circulation pump circulating the cleaning and disinfecting products contained in a tank that can receive at least one endoscope, this tank comprising injectors to which the endoscope channels can all be individually connected, said injectors being each coupled to the lower part of the hermetic chamber directed to a connecting pipe, an injection solenoid valve being arranged between the hermetic chamber and the injector on each of these connecting pipes.

BRIEF DESCRIPTION OF THE DRAWINGS

An example of embodiment is provided below, the general scope of which is not limited in any way by the particularities or to the particularities of the example selected for illustrative purposes.

In the attached drawing.

DETAILED DESCRIPTION OF THE PRESENT INVENTION

Figure 1:
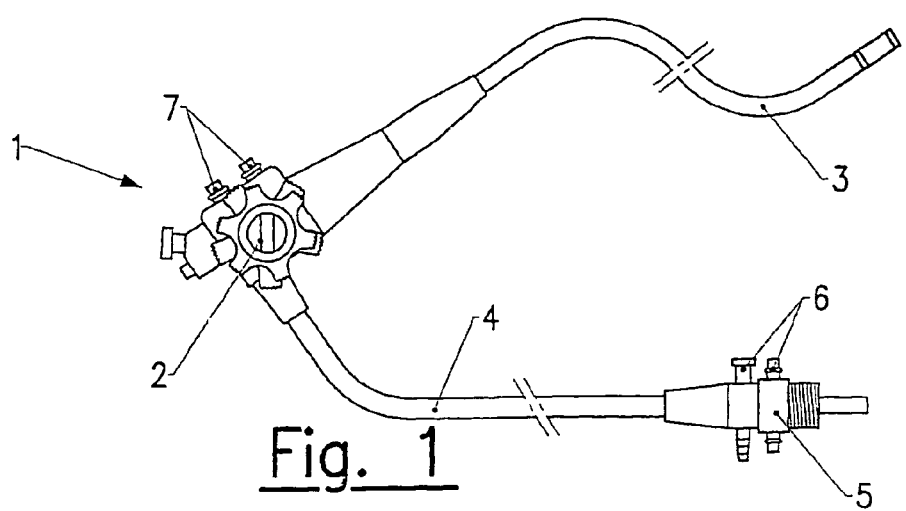
FIG. 1, previously mentioned, shows an endoscope of the common type.
Figure 2:
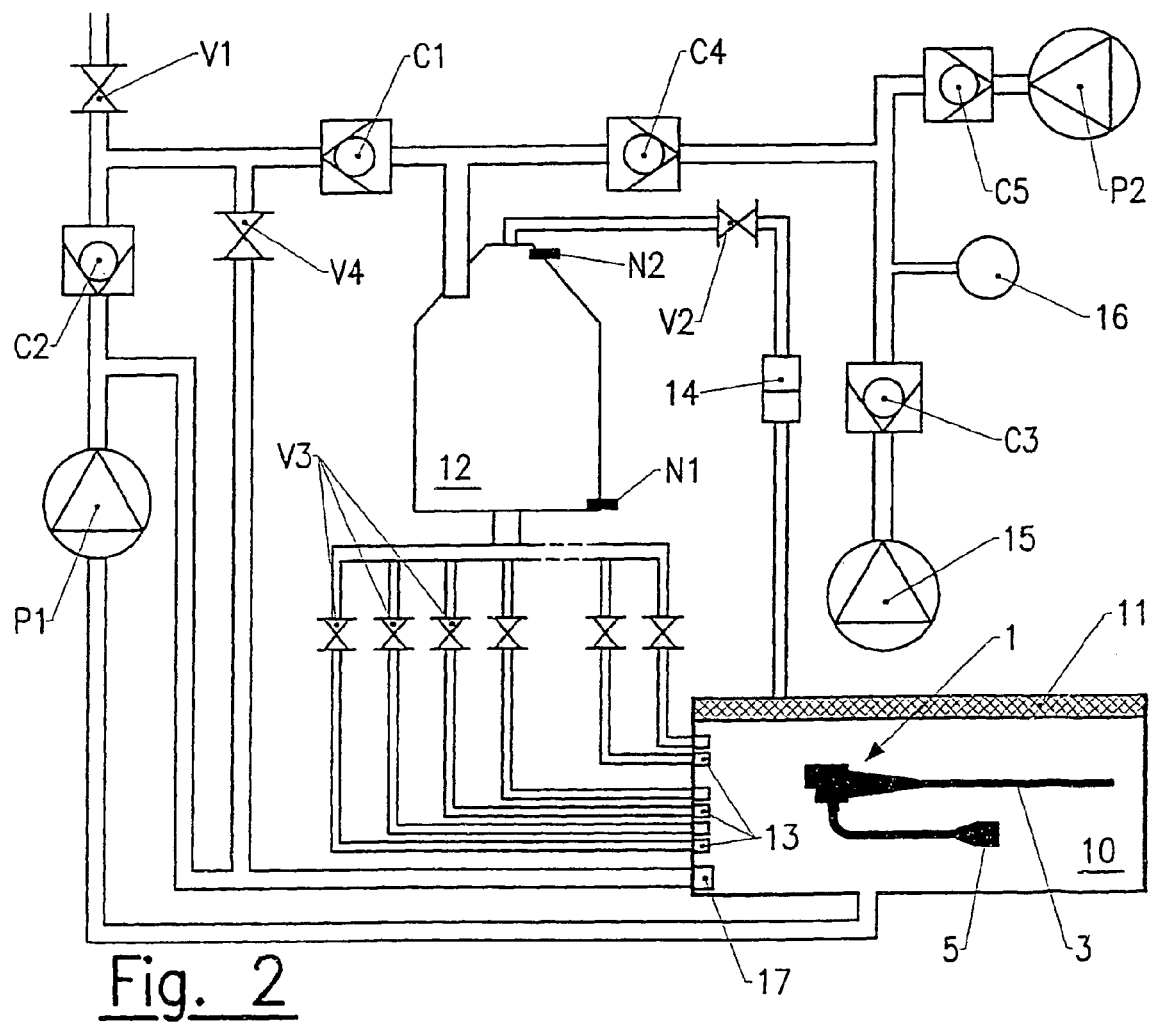
FIG. 2 is the synoptic diagram of a device according to the invention.

The present invention includes a tank 10 comprises a cap 11 equipped with an inflatable joint connected to a source of compressed air for ensuring that the assembly is impermeable once the cap is closed.

In particular, it comprises a circulation pump P1 that agitates the solutions in the tank 10 in which the endoscope 1 is positioned. Through two nonreturn valves C1, C2, this pump feeds a hermetic chamber 12 having a known volume that is preferably equal to at least one time the maximum volume of the largest channel of one endoscope.

The tank 10 is filled via solenoid valves V1, V4 connected to a rinsing water network. This water is filtered at 0.2 microns. The solenoid valves are connected to the hydraulic circuit coming from the circulation pump, between the valves C1 and C2.

A heating body allows heating the solutions prior to reinjecting them in the tank that is directed to two types of injectors 13, 13' making it possible, for some, to circulate the solutions around the outer portion of the endoscope 1, and for the others, to individually irrigate the inner channels of the apparatus.

The bottom of the tank is coupled to a drain pump that makes it possible to reject the solutions in the waste water network.

The unused injectors are coupled to tubes having an inner cross-section that is less than 5 mm, with a free end.

The top of the hermetic chamber 12 is coupled to a connection solenoid valve V2, the downstream portion is coupled to the tank 10, or to the cap 11 thereof, by means of quick connector 14 that can be easily accessed by the user from the outside of the machine, and which makes it possible to quickly and easily inject in the chamber, directed to a syringe or a pump, a solution, for example, a sampling solution, that can be collected after opening one or several solenoid valves at the end of one or several channels of the endoscope 1. The bottom of the chamber is coupled to the injection solenoid valves V3 which each are coupled to a special injector connector 13 in the tank, this connector being itself coupled to one of the inlets of the channels of the endoscope 1. A pump P2 for injecting a drying fluid (e.g., alcohol) is coupled for example by a nonreturn valve C5 to the line coming from the air compressor, between the valves C3 and C4.

The connection solenoid valve (V2) is coupled to the tank (10), or to the cap (11) of the tank, such that air and the solutions for filling the hermetic chamber (12) can return to the tank, either above or below the level of the fluid contained in said tank.

The hermetic chamber 12 is also equipped with a low level sensor N1 and a high level sensor N2.

A plurality of hermetic chambers having different volumes can be used together to control the flow of a plurality of endoscopes, or to more quickly control the flow in sets of channels of the same endoscope having similar diameters.

The system is equipped with a filtered air compressor 15 that feeds the hermetic chamber 12 at a given pressure through a line comprising a calibrated valve or two nonreturn valves C3, C4 between which a shunt pressure sensor 16 is inserted, and which makes it possible to control the pressure delivered in the chamber at different set values.

The cleaning and disinfecting products are injected in concentrated form in the tank 10 that is directed to an apportioning device. Next, they are diluted therein through agitation directed to the circulation pump P1. The standard cycle generally includes the following sequences:

Filling the tank
Injecting the cleaning product
Activating the circulation pump, cleaning the outer sheath of the endoscope and irrigating the endoscope channels
Draining the tank
Rinsing the tank and the endoscope channels with filtered water
Filing the tank
Injecting the disinfecting product
Activating the circulation pump, disinfecting the outer sheath of the endoscope and the endoscope channels
Draining the tank
Rinsing the tank and the endoscope channels with filtered water
Drying the channels All of the electromechanical components are guided by an automaton having a microprocessor which, depending on the state of the sensors (level, pressure, temperature), manages the cycle as well as an interruption alarm assembly.

The endoscopes 1 that are treated in this device comprise a label or a chip that makes it possible to feed the automaton that is directed to a reader with information about the mark of the endoscope, its serial number, as well as its type. The automaton has been programmed beforehand with data from the manufacturers of the endoscope regarding the length and diameter of the channels of which it is constituted.

For the connection to the inlets of the endoscope 1, separators are positioned beforehand in the piston cage 7 (FIG. 1) common to the air and water channels so as to separate the flows. These separators are machined so as to maintain a tiny communication between the two circuits that enables the disinfectant to act and not create any dead zone that cannot be disinfected. The communication should not permit a leakage greater than 30% of the flow in each of them.

For some of the endoscope channels, particularly those having an inner diameter greater than 3 mm, the coupling for connecting to the endoscope is equipped with a closing device that allows circulation only if the coupling is properly connected to the channel inlet.

Each of the inlets of the endoscope is coupled to a distinct injector 13 located in the tank 10 and capable of being identified for the coupling of at least one of the following channels: biopsy channel, suction channel, auxiliary biopsy channel or water jet channel, air channel, water channel, erecting channel, and auxiliary water channel.

Below is described the principle of controlling the irrigation of one of the channels with the solutions coming from the tank directed to the device according to the invention. This control is carried out in the following steps:

1. The state of the level sensors N1, N2 of the hermetic chamber 12 is verified. If the chamber is not empty, the air compressor 15 is activated at the same time as the channel solenoid valve V3 so as to empty the chamber.

2. As soon as the level sensors provide the adequate indication, the compressor 15 is activated until a set value (Pa) recorded in the automaton is reached by the pressure sensor 16.

3. A waiting time (TT) recorded in the automaton is observed. If, at the end of this time, the pressure in the chamber is still greater than (Pa−x), the control sequence is continued. Otherwise, an alarm indicates that there is a leakage in the circuit, and that the test cannot be properly conducted.

This operation makes it possible to ascertain that the hermetic chamber 12 and all of the channel solenoid valves V3 coupled thereto are impermeable prior to any filling.

The values (TT), (Pa), and (x) are determined as a function of the cross-sections and volumes of the circuits and of the hermetic chamber 12, so that the diagnosis time is optimized.

4. The connection solenoid valve V2 is open and the circulation pump P1 is activated so as to fill the hermetic chamber 12 with the solution coming from the tank 10. The time (T1) for reaching the high level (sensor N2) is timed and recorded in the automaton.

5. As soon as the high level sensor N2 indicates that the chamber is full, the action is maintained for a waiting time equal to half the filling time (T1/2) so as to ensure that the circuit is saturated up to the connection solenoid valve V2.

6. Simultaneously:
   the circulation pump P1 is deactivated
   the connection solenoid valve V2 is closed
   the solenoid valve V3 coupled to the channel to be controlled is opened
   the air compressor 15 is activated as long as the pressure indicated by the pressure sensor 16 does not exceed the maximum pressure (PM) authorized for the irrigation of the channel connected to the open channel solenoid valve V3.
   a timing is performed until the low level sensor N1 indicates that the chamber 12 is empty.

The value of the pressure (PM) to be applied in the chamber must make it possible to inject the confined solution volume in the chamber in the shortest time without however damaging the endoscope channels. It is comprised between 400 and 3,500 mbars depending on the channels.

7. Knowing the volume and the time makes it possible to determine the flow, to record it in a memory of the microprocessor and to compare it to a reference flow of an endoscope of the same type of this same channel, which had been previously recorded in the automaton at the factory (when the endoscope is known), or during the installation of the machine (if the endoscope is a less widely used model). The reference time obtained can advantageously be recorded in the automaton or in an external database connected to the automaton.

If the time is greater than the reference value increased by a coefficient (KB), it can be concluded that the channel is closed.

If the time is less than the reference value decreased by a coefficient (KD), one can conclude that the channel is disconnected, or that there is a leakage between the outlet of the solenoid valve V3 and the inlet of the endoscope channel.

In the case where the flows are within the prerecorded acceptable limit of the values, they are printed at the end of the cycle on the cycle validation card or transferred to a storage medium. Otherwise, the cycle is interrupted and a message indicates the cause as well as the channel from which the flaw originated.

8. If the endoscope 1 is provided with a bundle of channels having a common portion (e.g., biopsy and suction channel), the above sequence is repeated but by opening at step 5 all of the solenoid valves coupled to the channels having common portions with the channel to be treated, for example, the biopsy channel and suction channel.

9. Knowing the volume and the time makes it possible to determine the flow, to record it in a memory of the microprocessor and to compare it to a reference flow that is characteristic of the emptying of the hermetic chamber 12, simultaneously through all of the channels of the same chamber.

In the case where the flows are within the prerecorded acceptable limit of the values, they are printed at the end of the cycle on the cycle validation card or transferred to a storage medium. Otherwise, the cycle is interrupted, and a message indicates the cause as well as the channel from which the flaw originated.

If the time is less than the reference value decreased by a coefficient (KDG), it can be concluded that one of the channels in the bundle is disconnected, or that there is a leakage between the outlet of the solenoid valve V3 and the inlet of the endoscope channel.

10. At the end of the cleaning and disinfecting phases and during the emptying of the tank 10, the connection solenoid valve V2 and the solenoid valve V1 for filling the filtered water are opened for the time that is necessary for rinsing the chamber 12.

11. Next, the solenoid valves V1, V2 are closed and the compressor 15 is activated at the same time as the channel solenoid valves V3 are opened, until the level sensor N1 indicates that the chamber 12 is empty. The channels have thus been rinsed with clean water.

12. The compressor 15 is activated and the channel solenoid valves V3 are opened for the time that is necessary for draining the endoscope 1.

This flow control sequence in the channels is activated one or several times for all of the channels during each phase of the cycle, with the solution being present in the tank 10, namely:
   when filling the tank with water
   when cleaning
   when rinsing after cleaning when filling the tank 10 the second time
when disinfecting
when rinsing after disinfecting
when filling the tank 10 the third time
when rinsing During the periods where the control is not activated, all of the channel solenoid valves V3 are opened such that the flow coming from the filling solenoid valve V1 (irrigation with filtered water) or from the circulation pump P1 (irrigation with a cleaning or disinfecting solution) passes freely in the tank 10 to irrigate all of the channels.

The device also makes it possible to check a volume of drying fluid (e.g., alcohol) injected in the channels. To this end, the connection solenoid valve V2 and the drying fluid pump P2 are activated until the high level (sensor N2) of the chamber 12 is reached.

Next, the channel solenoid valves V3 and the air compressor 15 are opened until the low level sensor N1 indicates that the tank 10 is empty; then, for the time necessary for draining or evaporating the drying fluid.

At the end of the cycle, the cap 11 is opened, and samplings can be undertaken without it being necessary to disconnect the endoscope 1.

To this end, the quick coupling 14 is disconnected and the portion coming from the hermetic chamber 12 is coupled to the downstream portion of the body of a peristaltic pump. This body (silicone pipe) will have previously been sterilized. The upstream portion of the body of the pump is coupled to a sampling fluid flask. The distal end of the exploration tube 3 of the endoscope is inserted in a sterile sampling jar.

The operator can then select the channel to be sampled directed to touch keys on the data entry screen of the automaton. As long as the touch key is activated, the peristaltic pump and the solenoid valve V3 corresponding to the selected channel are activated. The sampling fluid pushed by the peristaltic pump comes back out through the end of the channel and is collected in the jar. Once the adequate quantity has been collected, the touch key is deactivated, and the sampling of the next channel can be undertaken.

A sequence can also be programmed to automatically sample one channel after the other.

The end of the endoscope is then removed from the collection jar, the quick coupling 14 connected to the machine, and a cycle is relaunched so as to rinse and disinfect the endoscope again.

The particularities appearing in the preceding description provide the invention with a maximum of useful effects that, until now, had not been obtained by similar devices or methods.

The invention claimed is:

1. A process for measuring and controlling the circulation of fluids in endoscope channels comprising:
    placing at least one endoscope into a tank;
    coupling one or more inlet channels of the endoscope to a hermetic chamber having a known volume and one or more valves, the hermetic chamber being equipped with a low level sensor and a high level sensor, and an upper portion of the hermetic chamber being connected to a connection solenoid valve that allows air to evacuate when the hermetic chamber is being filled;
    filling the hermetic chamber and valves to a high level position, thereby saturating the tank and inlet channels with a fluid from at least one fluid supply, wherein the filling is performed by a circulation pump arranged upstream of the hermetic chamber and which is configured to agitate contents of the tank;
    pressurizing the hermetic chamber using a filtered air compressor;
    controlling and recording a time for a fluid flow under pressure within the hermetic chamber to travel from the high level position to a designated low level position when at least one of the valves is open to at least a respective one of the one or more inlet channels; and
    confirming that the fluids are circulating in each portion of each channel of the endoscope, that the at least respective one of the one or more inlet channels are properly coupled to the at least one of the valves, and that none of the respective one or more channels are closed.

2. The process in accordance with claim 1, wherein the controlling occurs in a controller comprising the high level sensor and the low level sensor arranged to detect the emptying of the chamber, and
    wherein the controller verifies the known fluid volume and flow rate from a recorded emptying of the hermetic chamber, and uses the recorded fluid volume and flow rate in the confirming.

3. The process in accordance with claim 2,
    wherein the controller is able to control at the same time, the flow of several endoscopes using a plurality of hermetic chambers that have different volumes, as well as to increase the control of flow in sets of channels of the same endoscope having similar diameters.

4. The process in accordance with claim 1,
    wherein the controlling and filling of the hermetic chamber comprises:
    emptying of the hermetic chamber down to the low level under pressure, wherein a controller controls a filling time in the filling of the chamber up to the high level ensuring the valves, tank and channels of the endoscope are saturated with fluid; and
    emptying of the filled hermetic chamber and recording the time for the fluid to reach the low level.

5. The process in accordance with claim 4,
    wherein the controller compares the recorded emptying time of the fluid from the high level to the low level in the hermetic chamber to a reference time corresponding to an average time for emptying the chamber under the same pressure through the channel of an endoscope of the same type.

6. The process in accordance with claim 1,
    recording a reference time in a controller or in an external database connected to the controller so as to begin to establish a control time.

7. The process in accordance with claim 1,
    wherein a control time is repeated several times in a same channel of interest, such that an average of the measurements are compared to an independent reference time.

8. The process in accordance with claim 1,
    wherein a control time is undertaken in one or more steps of a fluid cycle comprising one of cleaning, disinfecting, rinsing, and drying.

9. The process in accordance with claim 1,
    wherein testing of the hermetic chamber operability comprises:
    purging the hermetic chamber and the one or more valves to verify the impermeability of the hermetic chamber and the one or more channel valves coupled thereto,
    filling the hermetic chamber to the high level; and
    pressurizing the hermetic chamber at a given pressure via the filtered air compressor under control of a sensor, such that a recorded measuring of a pressure drop during a specified period of time is sufficient to diagnose leakage.

10. The process in accordance with claim 1, further comprising testing of the operability of the high level sensor and the low level sensor of the hermetic chamber, wherein the measuring of time for filling the chamber between the low and high levels is recorded, and compares the recorded time to an independent reference time.

11. The process in accordance with claim 10,
wherein when the recorded time is greater or less, respectively, than the independent reference time, a cycle stop and/or an error message is generated.

12. The process in accordance with claim 1,
wherein the inlet channels of the endoscope are coupled to valves with connectors,
one or more separators are positioned and arranged at the inlet channels common to air and water channels so as to separate the flows of the air and water of an insufflation piston of the endoscope, and
the one or more separators allows a very slight communication between the air and the water channels preventing not greater than a 30% loss of flow for each of the channels, such that each of the channels of the endoscope are individually coupled to at least one individual injector located in the tank, along with being coupled to the hermetic chamber via at least one valve.

13. The process in accordance with claim 1, further comprising coupling injectors of the tank to a tube having an inner cross-section less than 5 mm, such that one end is free.

14. The process in accordance with claim 13,
wherein the endoscopes are coupled to the injectors by sealing couplings that permit fluid flow to pass only when the sealing couplings are properly connected to the inlet of the endoscope channel.

15. The process in accordance with claim 1, further comprising gathering at least one sample solution, wherein the endoscope channels are not disconnected at the end of a disinfecting cycle, and after selecting to open one or more injection valves, the sampling solution is injected through the connection valve using a pump or a syringe, such that the sampling solution is injected through the one or more channels of the endoscope, of which, the sampling solution is then collected at the end of the one or more channels end.

\* \* \* \* \*